US005470875A

United States Patent [19]

Merianos et al.

[11] Patent Number: 5,470,875
[45] Date of Patent: Nov. 28, 1995

[54] WATER SOLUBLE, ANTIMICROBIAL COMPOSITIONS OF POLYHEXAMETHYLENE BIGUANIDE AND IODOPROPYNYLBUTYL CARBAMATE

[75] Inventors: John J. Merianos, Middletown; Todd Elder, Florham Park; Paul Garelick, South Plainfield, all of N.J.

[73] Assignee: ISP Chemicals Inc., Chatham, N.J.

[21] Appl. No.: 369,600

[22] Filed: Jan. 6, 1995

[51] Int. Cl.⁶ .................. A01N 47/12; A61K 31/155; A61K 31/785; A61L 2/18
[52] U.S. Cl. ................ 514/479; 252/106; 422/28; 422/37; 514/478; 514/635; 514/840; 514/912
[58] Field of Search .............. 422/28, 37; 514/478, 514/479, 635, 840, 912

[56] References Cited

U.S. PATENT DOCUMENTS

| | | | |
|---|---|---|---|
| 4,758,595 | 7/1988 | Ogunbiyi | 514/635 |
| 5,073,372 | 12/1991 | Turner | 424/401 |
| 5,134,158 | 7/1992 | Whitekettle | 514/441 |
| 5,134,160 | 7/1992 | Whitekettle | 514/479 |
| 5,147,891 | 9/1992 | Donofrio | 514/479 |
| 5,162,343 | 11/1992 | Whitekettle | 514/345 |
| 5,200,421 | 4/1993 | Ludwig | 514/383 |
| 5,385,926 | 1/1995 | Ludwig | 514/383 |
| 5,389,300 | 2/1995 | Schmitt | 252/380 |
| 5,416,109 | 5/1995 | Donofrio | 514/479 |
| 5,422,073 | 6/1995 | Mowrey-McKee | 422/28 |

*Primary Examiner*—Dennis Albrecht
*Attorney, Agent, or Firm*—Walter Katz; Marilyn J. Maue; Joshua J. Ward

[57] ABSTRACT

A water soluble, antimicrobial composition having antifungal activity useful for disinfecting a contact lens comprise (a) polyhexamethylene biguanide and (b) iodopropynylbutyl carbamate, in a weight ratio of (a):(b) of at least 100:1.

3 Claims, No Drawings

WATER SOLUBLE, ANTIMICROBIAL COMPOSITIONS OF POLYHEXAMETHYLENE BIGUANIDE AND IODOPROPYNYLBUTYL CARBAMATE

BACKGROUND OF THE INVENTION

1. Field of the Invention

This invention relates to antimicrobial compositions, and more particularly, to water soluble, antimicrobial compositions of polyhexamethylene biguanide and iodopropynylbutyl carbamate, having antifungal activity, useful as disinfectant solutions for contact lenses.

2. Description of the Prior Art

Polymeric biguanides such as polyhexamethylene biguanide are known preservatives in aqueous disinfecting solutions used for cleaning contact lenses. While such solutions provide excellent antimicrobial activity, their antifungal activity is limited. Iodopropynylbutyl carbamate, on the other hand, has excellent antifungal activity; however, it is practically insoluble in water, dissolving only 156 ppm at 20° C.

Accordingly, it is an object of this invention to provide a water soluble, antimicrobial compositions of polyhexamethylene biguanide and iodopropynylbutyl carbamate, for use as disinfectant solutions for contact lenses.

SUMMARY OF THE INVENTION

A water soluble, antimicrobial composition having antifungal activity which is useful for disinfecting contact lenses is described herein. The compositions comprise (a) polyhexamethylene biguanide and (b) iodopropynylbutyl carbamate, in a weight ratio of (a):(b) of at least 100:1.

DETAILED DESCRIPTION OF THE INVENTION

What has been discovered herein is that water insoluble iodopropynylbutyl carbamate (IPBC) is rendered water soluble in the presence of a suitable amount of polyhexamethylene biguanide (PHMB). Normally, IPBC can be dissolved in water only to the extent of 156 ppm at 20° C. However, a combination of PHMB and IPBC, in a weight ratio of 100:1, will permit water dissolution of 2000 ppm of IPBC.

The compositions of the invention find particular utility in preserving contact lens solutions.

PHMB is commercially available as a 20% active solution under the trade names of Cosmocil® CQ (ICI), Vantocil® IB, Baquacil®. Other trade names for the same chemical are Polysept®, Phogucid® and Renew®. PHMB is a highly effective, nontoxic polymeric antimicrobial preparation; however, its antifungal activity against Aspergillus niger particularly is limited.

IPBC is also a commercially available antifungicidal product sold by Troy Chemical under the trade name of Troysan Polyphase® P100, which is 97% active 3-iodo-2-propynylbutyl carbamate.

EXPERIMENTAL

1. Preparation of Compositions of Invention

Experimental

EXAMPLE 1

| | |
|---|---|
| PHMB (Cosmocil® CQ) (20% active) (hydrochloride Salt) | 200.00 |
| IPBC (Troysan Polyphase® P100) (97% active) | 0.41 |
| Distilled water | 200.00 |
| | 400.41 gms |

The composition above was prepared by heating the PHMB solution to 50°–60° C. and adding the IPBC with stirring. Thereupon, most of the IPBC crystals went into solution upon the addition of 200 g of distilled water. The resulting clear solution was cooled to room temperature and the composition was tested for antibacterial and antifungal activity (10% active product).

EXAMPLE 2

| | |
|---|---|
| Phogucid® (20% active) (Phosphate Salt) | 200 g |
| IPBC (97% active) | 0.4 g |
| Water | 200 g |
| | 400 g |

Procedure: This composition was prepared in the same manner as Example 1. Upon cooling, a small, fine powder (15 mg) precipitated from solution; it was filtered before the solution was submitted for antimicrobial and antifungal activity.

2. Solubility of Synergistic Blends of 2% Aqueous Cosmocil® CQ and IPBC

TABLE A

| Cosmocil CQ:IPBC Percent Ratio | Cos CQ:IPBC Ratio | IPBC (ppm) | Water Solubility |
|---|---|---|---|
| 99.5:0.5 | 200:1 | 100 | Soluble |
| 99:1 | 100:1 | 200 | Soluble |
| 98.5:1.5 | 67:1 | 300 | Soluble |
| 97.5:2.5 | 40:1 | 500 | Insoluble |
| 90:10 | 10:1 | 2,000 | Insoluble |

3. Antimicrobial and Antifungal Activity

An in vitro Minimum Inhibitory Concentration (MIC) test was carried out in order to compare Cosmocil CQ and Phogucid with and without IPBC.

Trypticase soy broth (TSB) tubes were diluted for each test material to result in a final test concentration of 1.0%, 0.5%, 0.25%, 0.12%, 0.06%, 0.03%, 0.015%, 0.007%, and 0.003%.

Each dilution series was inoculated with these test organisms at the inoculum concentration listed.

| | | |
|---|---|---|
| *Staph. aureus* 6538 (SA) | | $1.82 \times 10^5$ cfu/ml |
| *E. coli* 8739 (EC) | | $1.0 \times 10^5$ cfu/ml |
| *Ps. aeruginosa* 9027 (PSA) | | $5.0 \times 10^4$ cfu/ml |
| *Ps. cepacia* 25416 (PSC) | | $4.4 \times 10^4$ cfu/ml |
| *C. albicans* 10231 (CA) | | $1.4 \times 10^4$ cfu/ml |
| *A. niger* 16404 (AN) | | $5.2 \times 10^3$ cfu/ml |

The bacterial TSB tubes were incubated for 24 hours at 37° C. The yeast and mold tubes were incubated for 48 hours at 27° C. The TSB tubes were examined for positive growth (cloudy tubes). The lowest concentration tested which had a clear (no growth) TSB tube is the static activity concentration.

After 24 hours incubation, the bacterial TSB tubes were streaked onto a neutralizing agar media, Letheen agar. A similar procedure was followed after 48 hours incubation with the fungal TSB tubes. The Letheen agar plates were incubated for 48 hours at the required temperature and then checked for growth. The cidal concentration is the lowest concentration exhibiting no growth.

The addition of IPBC to both Cosmocil® or Phoqucid® increased the antifungal activity of both compounds.

TABLE B

| | | Organism* | | | | | |
|---|---|---|---|---|---|---|---|
| | | SA | EC | PsA | PsC | CA | AN |
| (A) | 2% Cosmocil® | 600 | <70 | <70 | 600 | 600 | 5000 |
| (B) | 2% Cosmocial® CQ + 20 mg IPBC | <70 | <70 | <70 | 600 | 30 | 600 |
| (C) | 2% Phoqucid® | 1200 | <70 | <70 | 10000 | 5000 | 5000 |
| (D) | 2% Phoqucid® 20 mg IPBC | 600 | 150 | <70 | 5000 | 300 | 300 |

Table A gives the cidal activity in ppm for each organism for the four test samples.

What is claimed is:

1. A water soluble antimicrobial composition having antifungal activity useful for disinfecting a contact lens comprising (a) polyhexamethylene biguanide and (b) iodopropynylbutyl carbamate, in a weight ratio of (a):(b) of at least 100:1.

2. An aqueous ophthalmic composition comprising (a) 99.9 to 99.0 weight percent of polyhexamethylene biguanide as an antimicrobial agent and (b) 0.1% to 1% weight percent of iodopropynylbutyl carbamate, as an antifungal agent.

3. An aqueous antimicrobial composition having antifungal activity comprising (a) polyhexamethylene biguanide and (b) iodopropynylbutyl carbamate, in a weight ratio of (a):(b) of at least 100:1.

* * * * *